(12) United States Patent
Kadobayashi et al.

(10) Patent No.: US 8,562,350 B2
(45) Date of Patent: *Oct. 22, 2013

(54) SET OF ARTIFICIAL TEETH OF ANTERIOR TEETH LINEARLY CONTACTING WITH EACH OTHER

(75) Inventors: Yusei Kadobayashi, Kyoto (JP); Toshihide Fujii, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 694 days.

This patent is subject to a terminal disclaimer.

(21) Appl. No.: 12/634,924

(22) Filed: Dec. 10, 2009

(65) Prior Publication Data

US 2010/0151418 A1    Jun. 17, 2010

(30) Foreign Application Priority Data

Dec. 16, 2008  (JP) .................................. 2008-319121
Oct. 8, 2009   (JP) .................................. 2009-234292

(51) Int. Cl.
*A61C 13/10* (2006.01)
(52) U.S. Cl.
USPC .......................................... 433/196; 433/171
(58) Field of Classification Search
USPC ................. 433/167–172, 182–183, 191, 195, 433/196–198, 199.1, 202.1
See application file for complete search history.

(56) References Cited

U.S. PATENT DOCUMENTS

| 1,753,644 | A  | * | 4/1930 | Burden          | 433/181 |
| 2,028,882 | A  | * | 1/1936 | Swan et al.     | 433/183 |
| 3,252,220 | A  |   | 5/1966 | Goddard         |         |
| 4,661,068 | A  | * | 4/1987 | Harrison et al. | 433/181 |
| 6,079,981 | A  | * | 6/2000 | Sekendur        | 433/171 |
| 2009/0117518 | A1 | * | 5/2009 | Massad      | 433/171 |

FOREIGN PATENT DOCUMENTS

JP    6-261917    9/1994

OTHER PUBLICATIONS

Notice of Reason for Rejection (in English language) issued Feb. 9, 2010 in corresponding to Japanese Patent Application No. 2009-234292.

\* cited by examiner

*Primary Examiner* — Cris L Rodriguez
*Assistant Examiner* — Edward Moran
(74) *Attorney, Agent, or Firm* — Wenderoth, Lind & Ponack, L.L.P.

(57) ABSTRACT

In a set of artificial teeth, at least one of mutually adjacent artificial anterior teeth includes abutting faces which contacts linearly with the other one so as to form abutting lines and capable of continuously moving the positions of the linear contact, the abutting faces being formed of any one of circular columnar surface, elliptical columnar surface, and conical surface.

7 Claims, 10 Drawing Sheets

SET OF ARTIFICIAL TEETH OF ANTERIOR TEETH LINEARLY CONTACTING WITH EACH OTHER

BACKGROUND OF THE INVENTION

1. Field of the Invention

The present invention relates to a set of artificial teeth.

2. Description of the Related Art

Conventionally, artificial teeth for manufacturing a dental prosthetic appliance (a plate denture) have been designed with a special emphasis on the appearance so as to be as similar to natural teeth as possible. Natural teeth are gradually smaller in width toward the cervical area as seen from the labial side as shown in FIG. 22, and mutually adjacent teeth contact with each other only at one point close to the incisal edge.

When manufacturing a dental prosthetic appliance, the dental technician needs to determine the angle around the long axis while paying attention so as not to incline this long axis (dental axis), and arrange so as to contact with the adjacent artificial teeth, requiring an advanced skill and enough experience. For the ease of arrangement of artificial teeth, an invention for coupling artificial teeth mutually has been disclosed, for example, in JP-A-06-261917.

The shape of the jaw varies significantly from a patient to another, the width size of the dental arch varies about plus or minus 6 mm from the standard size. Conventionally, plural types of sets of artificial teeth of different width sizes have prepared, and the dental technician has been selected and used the set of artificial teeth closest to the width size of the patient.

Moreover, the shape of the teeth varies from a patient to another, some giving an impression of wide or long image in a long axis direction, or others giving an impression of round or square image. As a result, a wide variety of sets of artificial teeth are provided to conform to various width sizes and to various aesthetic shapes.

Thus, the dental technician needs to select a most appropriate set of artificial teeth from a wide variety of sets of artificial teeth according to the condition of a specific patient. Preparation of a wide variety of sets of artificial teeth incurs relatively high, it adds to the cost of the individual set of artificial teeth.

SUMMARY OF THE INVENTION

In the light of the problems discussed above, it is an object of the present invention to provide a set of artificial teeth easy in arrangement, and applicable to multiple patients by using one kind only.

To achieve the above object, the present invention provides a set of artificial teeth, wherein at least one of mutually adjacent artificial anterior teeth includes abutting faces which contacts linearly with the other one and capable of continuously moving the positions of the linear contact.

With this configuration, mutually adjacent artificial anterior teeth linearly contact with each other, so that the direction of mutual dental axes is determined, the dental technician can arrange the artificial anterior teeth without paying attention to the inclination of dental axes of the artificial anterior teeth. On the other hand, by shifting the contact position of one artificial anterior tooth, the curvature of the dental arch can be changed, and the width size can be adjusted.

In the set of artificial teeth of the present invention, the abutting faces may be formed of any one of circular columnar surface, elliptical columnar surface, and conical surface.

With this configuration, a linear contact of an effective length can be realized, even if the position is deviated, in a simple shape.

In the set of artificial teeth of the present invention, the abutting faces may be formed as being extended nearly up to the basal surface of the artificial anterior teeth.

With this configuration, in the plate denture, since the abutting face is extended to the portion concealed by the interdental papilla, even if the efficiency of arrangement is enhanced by extending the contact length of adjacent teeth, the appearance is not different so much from the natural teeth.

In the set of artificial teeth of the present invention, the abutting faces may be formed as being away from the cutting edges of artificial anterior teeth.

With this configuration, the shape at both sides in a mesio-distal direction near the cutting edge of artificial anterior teeth has a significant effect on the aesthetic impression, and by forming the abutting face at a position distant from the cutting edge, both the natural appearance of artificial teeth and the high efficiency of arrangement can be satisfied.

In the set of artificial teeth of the present invention, the abutting faces may be extended from the labial side to the lingual side of the artificial anterior teeth.

With this configuration, the possible relative angle range of adjacent artificial anterior teeth is large, and the adjustable range of width size of the dental arch is wide.

According to the present invention, since adjacent artificial anterior teeth linearly contact with each other, the adjacent artificial teeth determine the dental axes with each other, and the relative angle can be adjusted by shifting the contact position of the mutually adjacent artificial teeth, so that the width size of the dental arch can be adjusted.

BRIEF DESCRIPTION OF THE DRAWINGS

An embodiment of the present invention is described below with reference to the accompanying drawings, in which.

DESCRIPTION OF THE INVENTION

Figure 1:
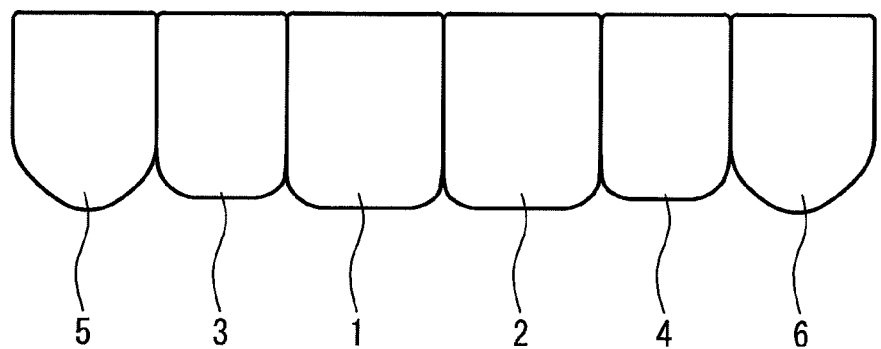
FIG. 1 is a view of a set of artificial teeth as seen from a labial side in a first embodiment of the present invention.

FIG. 1 is a view of a set of artificial teeth in a first embodiment of the present invention. This embodiment is a set of artificial maxillary anterior teeth including upper right and left central incisors 1, 2, lateral incisors 3, 4, and canines 5, 6.

Figure 2:
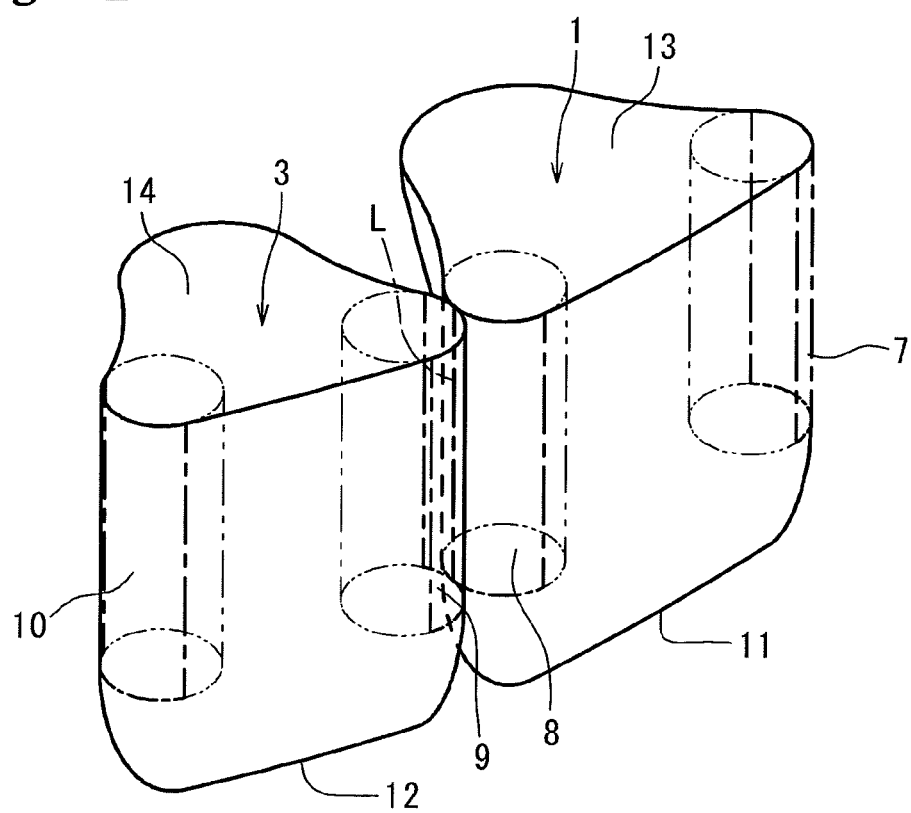
FIG. 2 is a perspective view of right central incisor and right lateral incisor of the set of artificial teeth of FIG. 1.

Common features of the artificial anterior teeth 1, 2, 3, 4, 5, 6 of the embodiment are explained while referring to a representative example of the artificial right central incisor 1 and the artificial right lateral incisor 3 in FIG. 2. The artificial anterior teeth 1, 3 are respectively provided with abutting faces 7, 8 and 9, 10 formed by a part of a circular columnar surface parallel to the dental axis at both sides in the mesio-distal direction. The abutting face 8 of the artificial central incisor 1 and the abutting face 9 of the artificial lateral incisor 3 linearly contact with each other, so that an abutting line L extended parallel to the dental axis is formed.

The abutting faces 7, 8, 9, 10 are extended from positions distant from cutting edges 11, 12 of the artificial anterior teeth 1, 3, up to basal surfaces (upper end faces) 13, 14. The abutting faces 7, 8, 9, 10 are also extended from the labial side to the lingual side of the artificial anterior teeth 1, 3, respectively.

Figure 3:
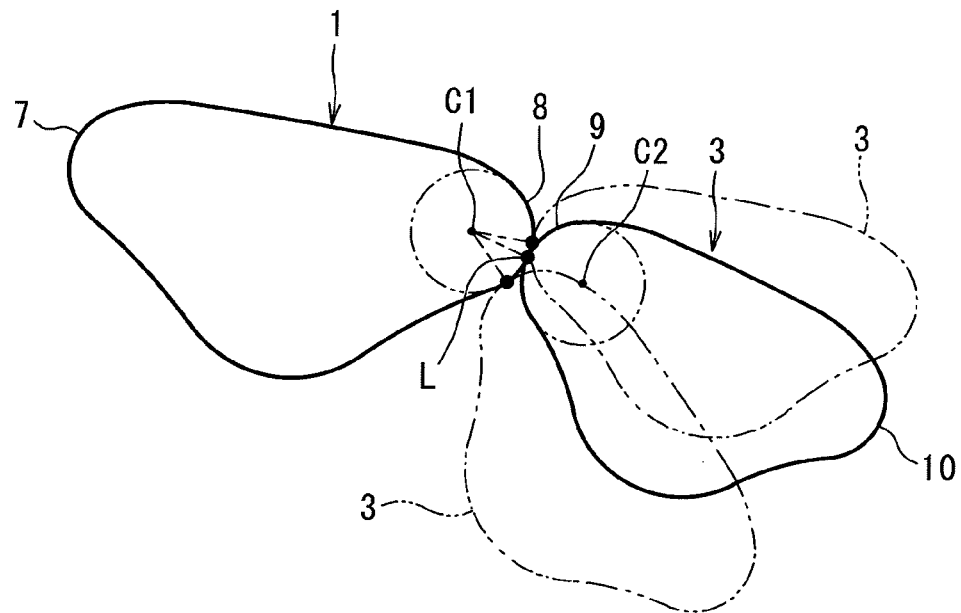
FIG. 3 is a view of the right central incisor and the right lateral incisor as seen from the basal surface side.

As shown in FIG. 3, the artificial lateral incisor 3 has the abutting face 9 capable of abutting on any desired position of the abutting face 8 of the artificial central incisor 1. Specifically, the artificial lateral incisor 3 can rotate about a central axis C1 of the circular columnar surface forming the abutting face 8 of the artificial central incisor 1, while forming the abutting line L of a specified length in the dental axial direction.

The artificial central incisor 1 also can rotate about a central axis C2 of the circular columnar surface forming the abutting face 9 of the artificial lateral incisor 3. This motion is seen while the artificial central incisor 1 is fixed, and as shown in FIG. 4, it is understood that the artificial lateral incisor 3 rotates about the central axis C2 of the circular columnar surface forming the own abutting face 9.

Figure 4:
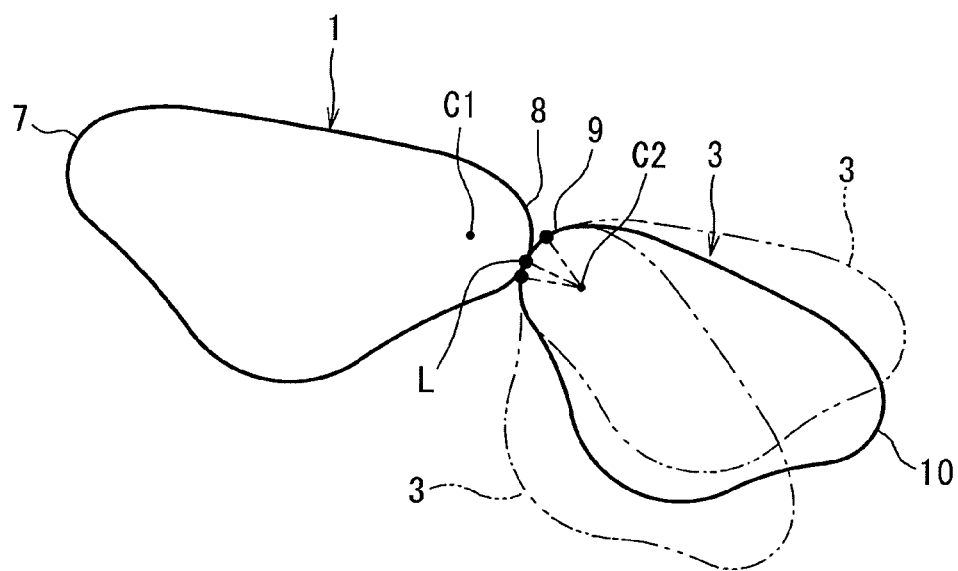
FIG. 4 is a view of the right lateral incisor of FIG. 3 being rotated along the right central incisor.
Figure 5:
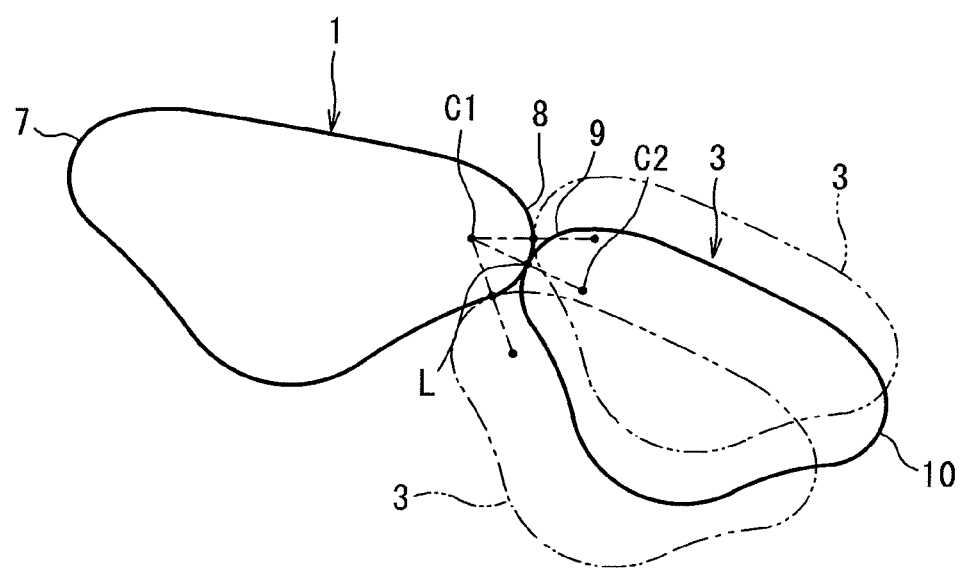
FIG. 5 is a view of the right lateral incisor of FIG. 3 being rotated on its axis.

The move of the artificial lateral incisor 3 as shown in FIG. 3 and the move as shown in FIG. 4 can be combined. For example, as shown in FIG. 5, the artificial lateral incisor 3 can be moved in parallel while holding its attitude without changing the angle around the dental axis, while its abutting face 9 is contacting with the abutting face 8 of the artificial central incisor 1. Moreover, the abutting face 9 of the artificial lateral incisor 3 can be rolled without slipping on the abutting face 8 of the artificial central incisor 1.

Figure 6:
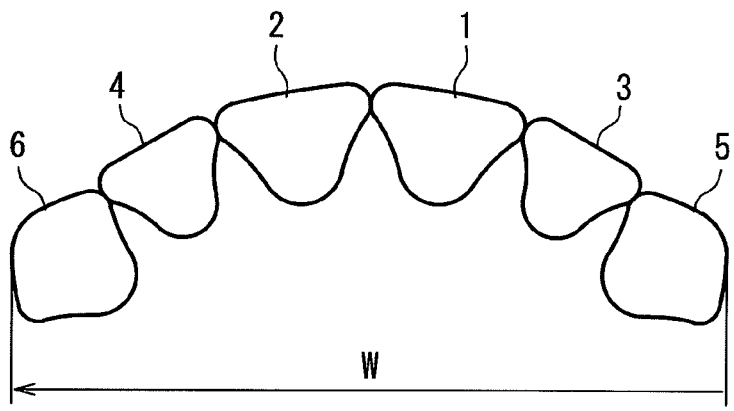
FIG. 6 is a view of right lateral incisor of FIG. 3 moved in parallel along the right central incisor.
Figure 7:
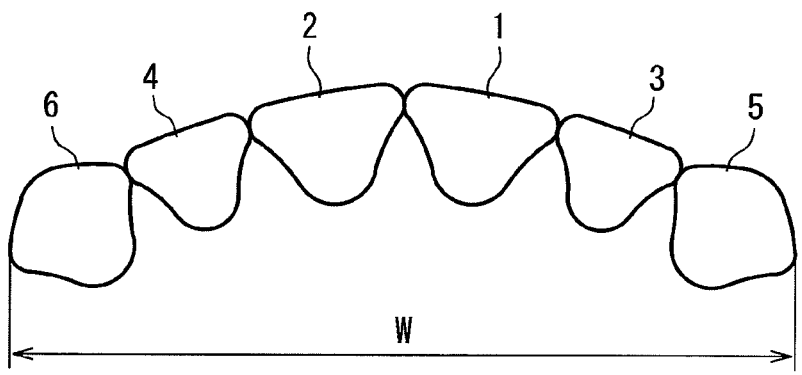
FIG. 7 is a view of the dental arch of the set of artificial teeth of FIG. 1.
Figure 8:
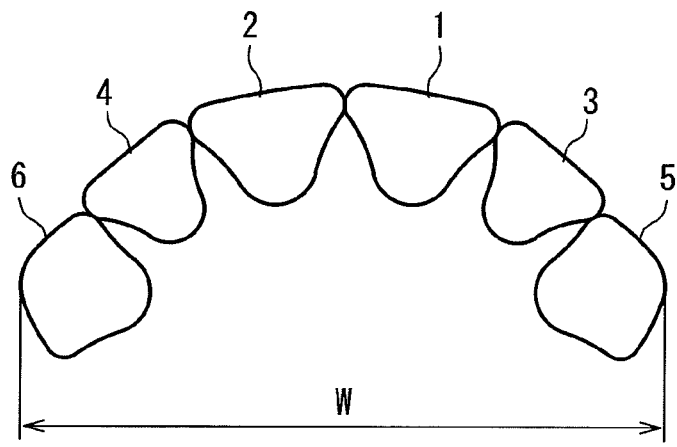
FIG. 8 is a view of distal side artificial anterior teeth of FIG. 7 reduced in width size by rolling to the mesial side artificial anterior teeth.

FIG. 6 shows an arrangement of the design of the set of artificial teeth of the embodiment along the dental arch. In the set of the artificial teeth in this state, a width W between both ends of the right and left artificial canines 5, 6 is about 51 mm, which corresponds to an average of distance between both ends of right and left canines of an adult human. The distance between both ends of right and left canines in adult human ranges from about 45 mm to about 67 mm, and there is a significant individual difference, and the fluctuation is about plus or minus 6 mm from the standard state. In the set of the artificial teeth of the embodiment, by rolling the abutting face of the mesial side of the artificial anterior tooth at the distal side of the mutually adjacent artificial anterior teeth on the abutting face of the distal side of the artificial anterior tooth of the mesial side, the width size of the dental arch can be expanded as shown in FIG. 7 in which the width W between both ends of right and left artificial canines 5, 6 is expanded by 6 mm or more, or the width size of the dental arch can be shortened as shown in FIG. 8 in which the width W between both ends of right and left artificial canines 5, 6 is shortened by 6 mm or more. In other words, the set of the artificial teeth of the embodiment can be suited to the alveolar ridge shape of almost all patients by freely setting the width W between both ends of right and left artificial canines 5, 6.

Figure 9:
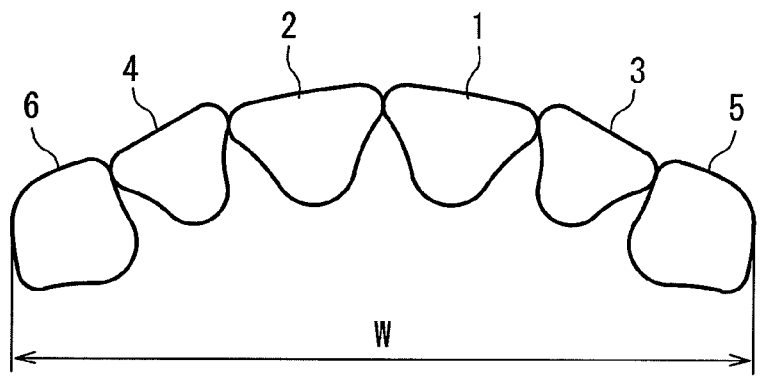
FIG. 9 is a view of the distal side artificial anterior teeth of FIG. 7 enlarged in width size by rolling to the mesial side artificial anterior teeth.
Figure 10:
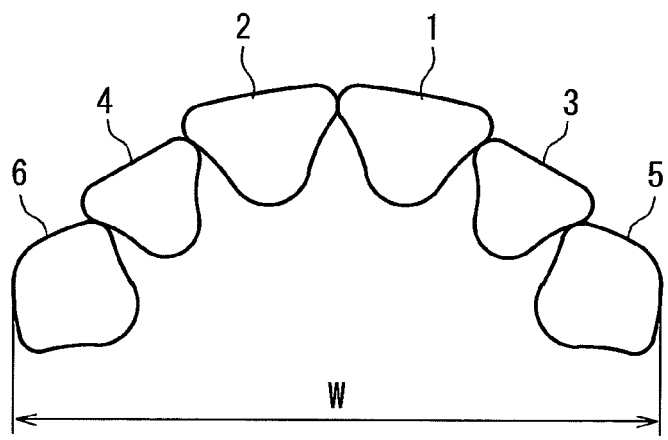
FIG. 10 is a view of the distal side artificial anterior teeth of FIG. 7 reduced in width size by moving in parallel along the mesial side artificial anterior teeth.

Moreover, in the set of the artificial teeth of the embodiment, by moving the artificial anterior tooth of the distal side of mutually adjacent artificial anterior teeth in parallel while contacting between the mutual abutting faces, the width size of the dental arch can be expanded by 6 mm or more as shown in FIG. 9, or the width size of the dental arch can be shortened by 6 mm or more as shown in FIG. 10.

Figure 11:
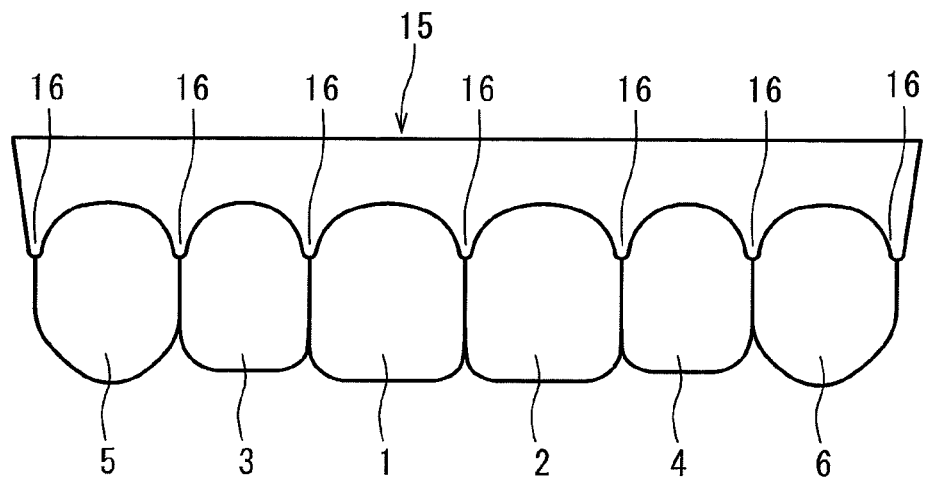
FIG. 11 is a view of the distal side artificial anterior teeth of FIG. 7 enlarged in width size by moving in parallel along the mesial side artificial anterior teeth.

When only the set of the artificial teeth of the embodiment is observed, the extending shape of the abutting faces 7, 8, 9, 10 nearly up to the basal surface is largely different from that of the natural teeth, and a very strange impression may be given. However, in the plate denture, as shown in FIG. 11, the basal surface side portion of the abutting faces is concealed by an interdental papilla 16 formed in a dental plate 15, and the appearance is not so much different from the natural teeth.

Therefore, the abutting faces of the invention are preferably extended as close to the basal surface as possible, and by forming a long contact line higher than the artificial teeth by 30% or more, or 60% or more preferably, the adjacent artificial anterior teeth support with each other, so that the inclination of the mutual dental axes may be prevented. In the embodiment, the boundary of basal surface and the abutting faces is only slightly chamfered, and substantially the abutting faces are extended up to the basal surface.

In the present invention, in order to realize the aesthetic impression of artificial anterior teeth as closely to natural teeth as possible, the abutting faces are formed at a position distant from the cutting edges at a distance of at least 5% or more of the height of the artificial anterior teeth in the dental axial direction, so that the shape in the vicinity of cutting edges to determine the impression of anterior teeth may be designed freely. As a result, the shape at both sides in the mesial and distal direction of the cutting edges of the artificial anterior teeth is designed freely, and thereby either a round impression or a square impression may be given.

Figure 12:
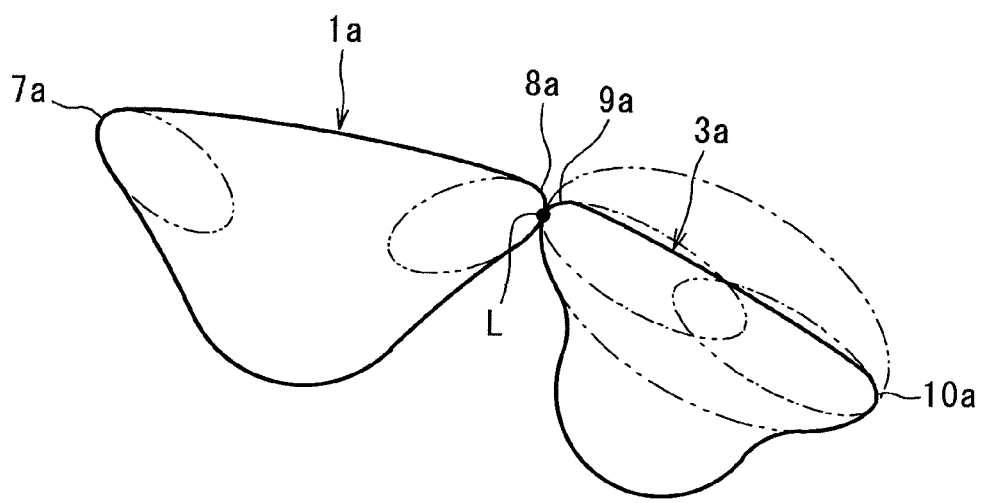
FIG. 12 is a view of right central incisor and right lateral incisor of a set of artificial teeth in a second embodiment of the present invention as seen from the basal surface side.
Figure 13:
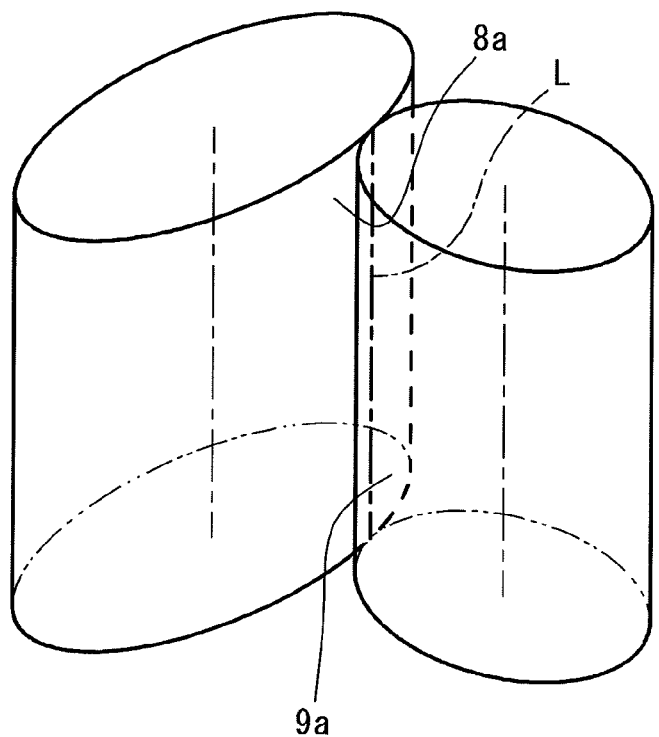
FIG. 13 is a schematic view of elliptical central surface for forming the abutting face of the right central incisor and the right lateral incisor of FIG. 12.

FIG. 12 shows an artificial central incisor 1a and an artificial lateral incisor 3a of a set of artificial teeth in a second embodiment of the present invention. The artificial teeth 1a, 3a of the embodiment are provided with abutting faces 7a, 8a, 9a, 10a formed of an elliptical columnar surface. As shown in FIG. 13, mutually parallel elliptical columns linearly contact with each other so as to form abutting lines L parallel to the central axis and having a length equal to the height of the both, at arbitrary outer circumferential positions of the both. In other words, the artificial teeth 1a, 3a having the abutting faces 7a, 8a, 9a, 10a formed of an elliptical columnar surface can move or roll along the mutual abutting faces.

In the artificial lateral incisor 3a shown in FIG. 12, the curvature of the elliptical columnar surface for forming the abutting faces 9a, 10a is changed midway. Thus, in the present invention, the circular columnar surface or the elliptical columnar surface for forming the abutting faces may be varied in the curvature midway. The elliptical columnar surface may be assumed to be a set of circular columnar surfaces varied continuously in the curvature. Further, a flat plane may be formed by setting the circular columnar surface at an infinite curvature, or an angle may be formed by setting the circular columnar surface at zero curvature. In other words, the abutting faces of the present invention only need to be formed at least a part of the outer circumferential surface of a columnar body having a fixed sectional shape, and the sectional shape of the columnar body is not particularly limited.

Figure 14:
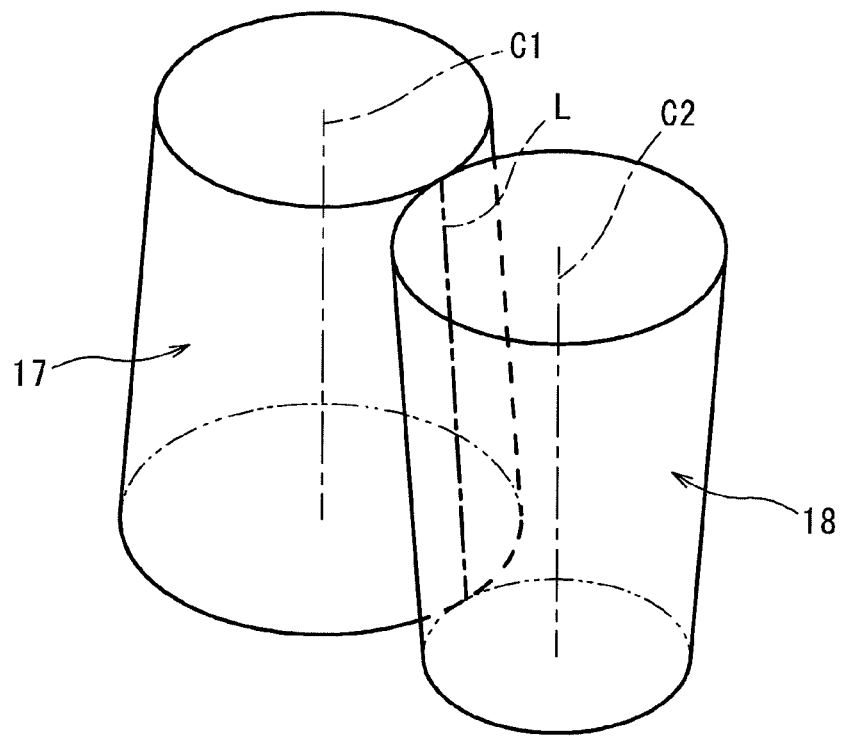
FIG. 14 is a schematic view of a pair of conical surfaces for forming the abutting face of the present invention.

Moreover, the abutting faces of the present invention may be also formed of conical surfaces 17, 18 having central axes C1, C2 parallel to the dental axis as shown in FIG. 14. As shown in the figure, the two conical surfaces 17, 18 for forming abutting lines L of a specific length by linearly contacting with each other are mutually inclined complementarily on the surfaces.

Figure 15:
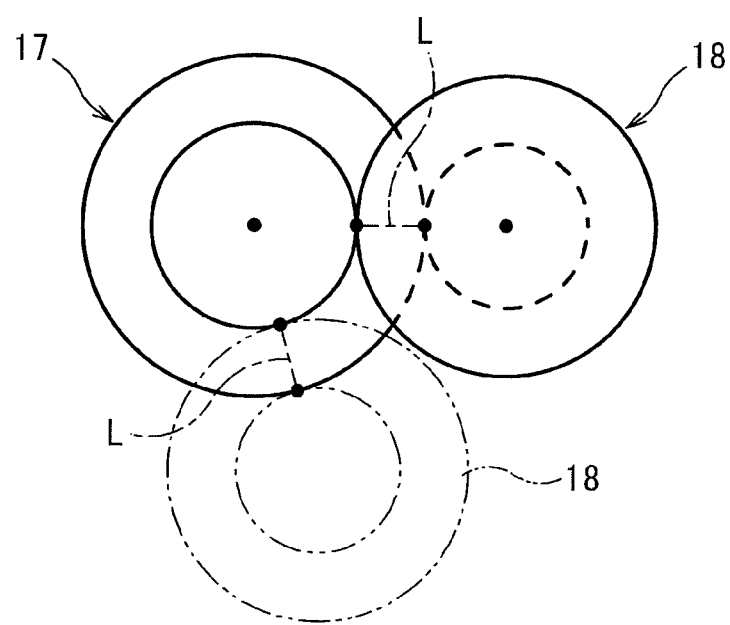
FIG. 15 is a plan view of the pair of conical surfaces of FIG. 14.

FIG. 15 is a view of the conical surfaces 17, 18 of FIG. 14 as seen from the upside in the dental axial direction. As shown in the figure, the two conical surfaces 17, 18 abut on each other at arbitrary outer circumferential positions, so that the edges of the upper bottoms and the edges of the lower bottoms of the two conical surfaces respectively abut each other and a linear abutting line L linking the two abutting point of the edges is formed.

Figure 16:
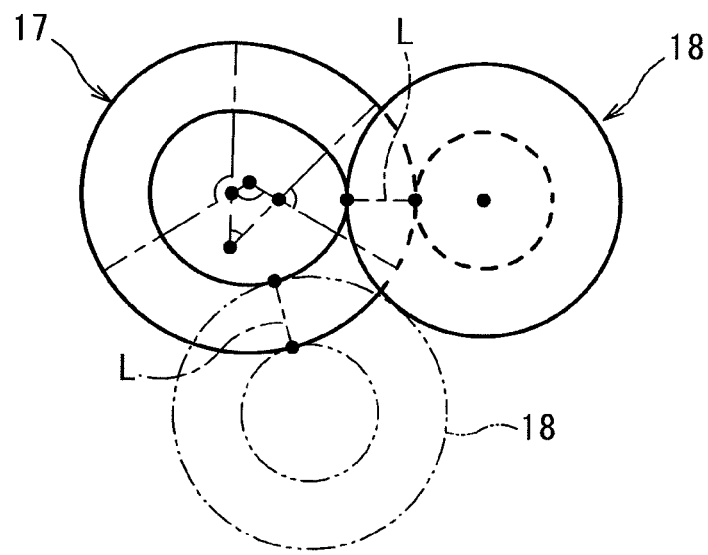
FIG. 16 is a plan view of the pair of conical surfaces varied midway in the curvature.
Figure 17:
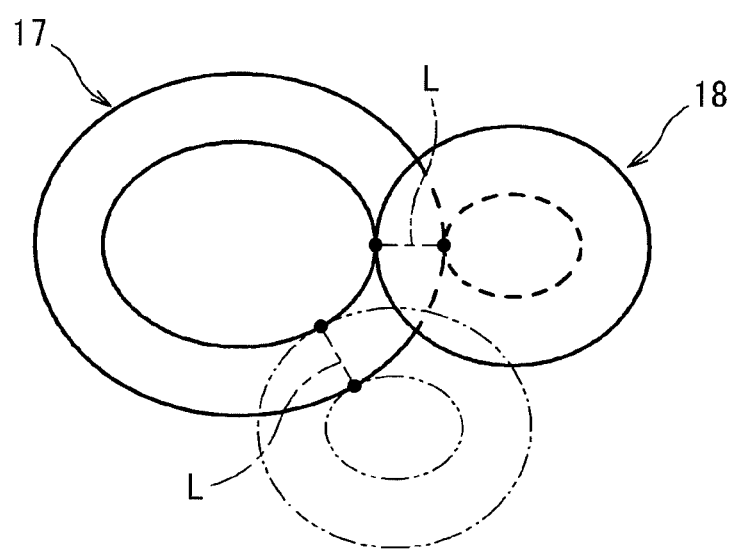
FIG. 17 is a plan view of the pair of conical surfaces varied in the curvature continuously so as to have an elliptical bottom.
Figure 18:
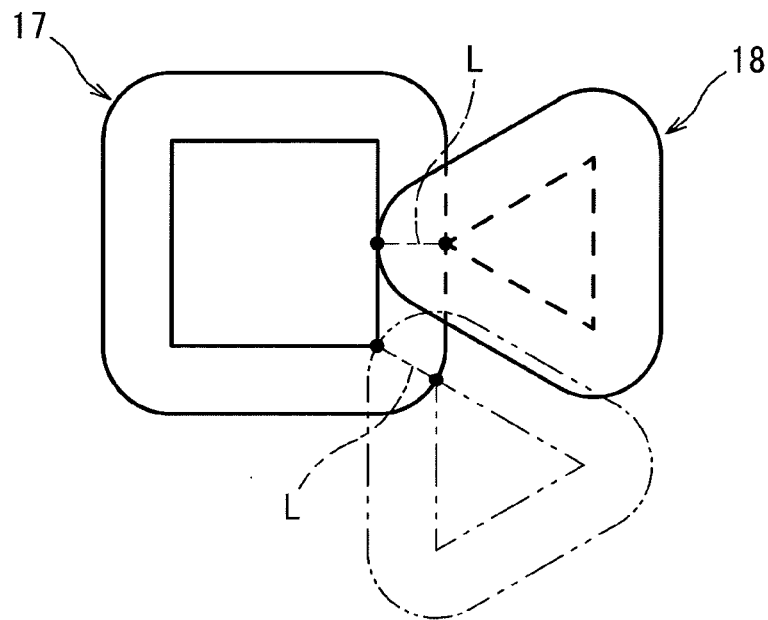
FIG. 18 is a plan view of the pair of conical surfaces having a partially infinite curvature.

According to the present invention, as shown in FIG. 16, the curvature of the conical surfaces 17, 18 can be changed midway. Alternatively, as shown in FIG. 17, by using conical surfaces 17, 18 changed continuously in the curvature, the abutting faces of the artificial anterior teeth may be formed of tapered curved surfaces specific in the inclination angle of the elliptical shape in the bottom, or as shown in FIG. 18, the abutting faces of the artificial anterior teeth may be formed also of a combination of curved surfaces of conical surfaces having a fixed inclination angle and flat surfaces (circular cones of infinite curvature).

Figure 19:
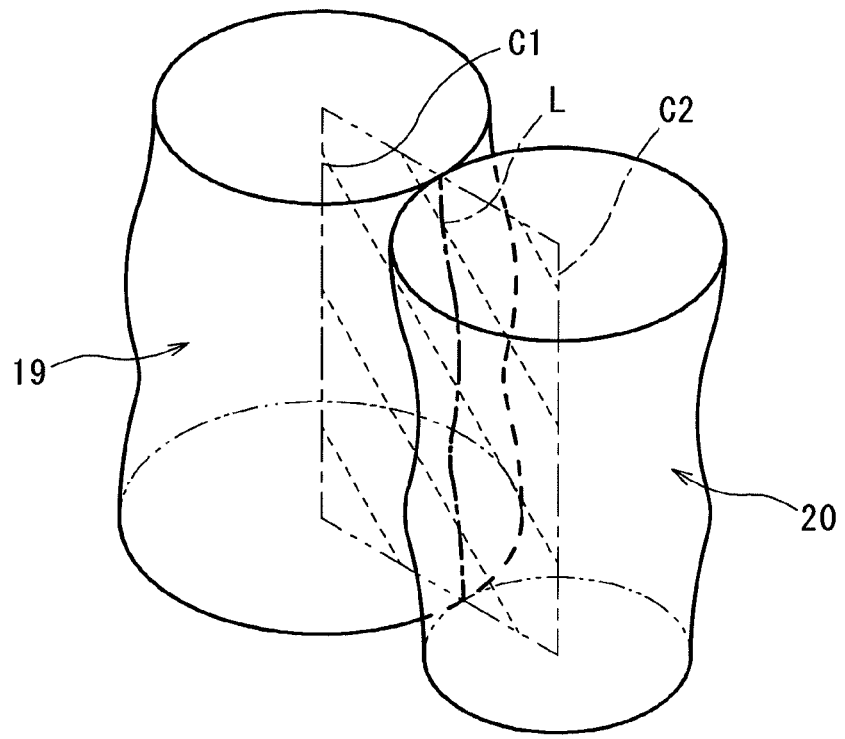
FIG. 19 is a schematic view of a pair of rotary elements of free curved lines for forming the abutting face of the present invention.

Further, according to the present invention, as shown in FIG. 19, the abutting faces of the artificial teeth may be formed of rotating body surfaces having the abutting lines L of free curved lines rotated about the central axis parallel to the dental axis. In this case also, the curvature may obviously be changed freely.

In addition, there is a geometrical principle, that is, two mutually contacting curved surfaces always coincide in the normal of two curved surfaces at a contacting position. When one curved surface is moved by slipping on the other curved surface, the slipping and moving direction is the direction orthogonal to the normal at the contacting point. Accordingly, the normal at all points on the abutting line L must be perpendicular to the rotating direction of the abutting line L. In the present invention, the width size of the dental arch must be adjusted by slipping and moving the artificial anterior teeth in a direction orthogonal to the dental axis along the adjacent artificial anterior teeth, but if the abutting line L includes a point different in angle about the central axes C1, C2, the abutting line L can be rotated unless the curvature is infinite, and the object of the present invention is not achieved. Hence, the abutting line L in the present invention must be a line involved by a flat surface including the central axes C1, C2.

Figure 20:
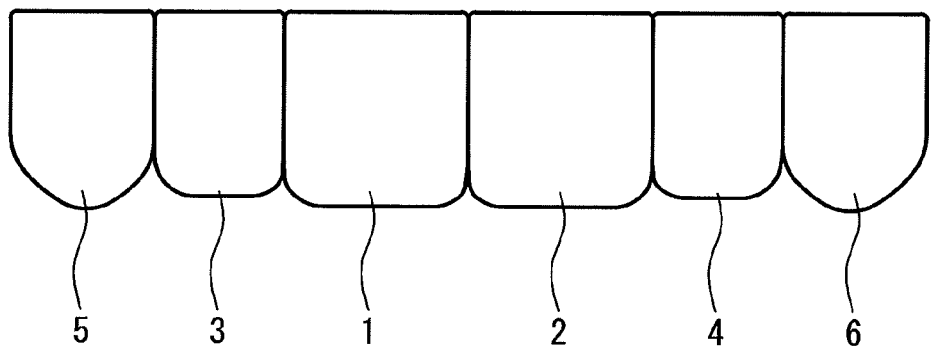
FIG. 20 is a view of the set of artificial teeth of FIG. 1 changed in the shape of incisors as seen from the labial side.
Figure 21:
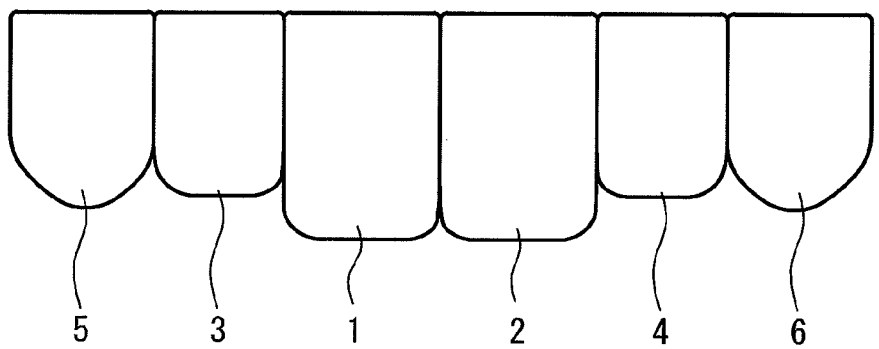
FIG. 21 is a view of the set of artificial teeth of FIG. 1 changed further in the shape of incisors as seen from the labial side.
Figure 22:
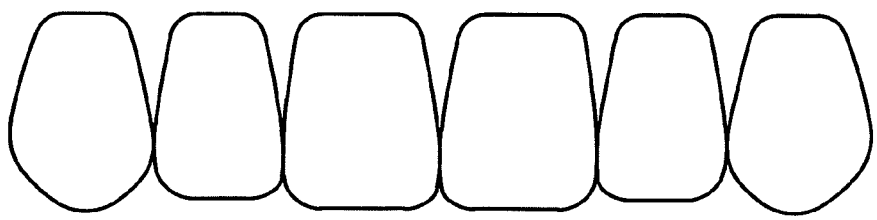
FIG. 22 is a view of a set of artificial teeth in prior art seen from the labial side.

Further, according to the invention, in order to present dental prosthetic appliances of different aesthetic impressions, for example, only the upper central incisors 1, 2 may be replaced with substitutes of different shapes as shown in FIG. 20 and FIG. 21. In the oral cavity, the aesthetic impression of teeth is determined mostly by the two upper central incisors.

Therefore, according to the invention, by presenting only one set of artificial teeth having abutting faces, and exchangeable upper central incisors having similar abutting faces, any dental arch suited to the alveolar ridge shape of almost all patients can be formed, and the dental prosthetic appliance having an aesthetic impression suited to the patient can be manufactured.

The present invention may obviously be also applied in artificial mandibular anterior teeth, and further a set of artificial teeth including molar teeth may be also presented.

What is claimed is:

1. A set of artificial teeth comprising:
a plurality of artificial anterior teeth, at least a first artificial anterior tooth of the plurality of artificial anterior teeth being positioned adjacent at least a second artificial anterior tooth of the plurality of artificial anterior teeth when arranged on a denture plate, wherein the first artificial anterior tooth of the artificial anterior teeth includes an abutting face, the abutting face being an integral area of an outer surface of the first artificial anterior tooth, and the abutting face contacting the second artificial anterior tooth so as to form a contact line on the abutting face when the first and second artificial anterior teeth are arranged on the denture plate and the first and second artificial anterior teeth being capable of being moved relative to each other such that the position of the contact line is moved along the abutting face, so as to determine a position of a dental axis of the first artificial anterior tooth relative to the second artificial anterior tooth when arranging the plurality of artificial teeth on the denture plate, and
wherein the abutting face is formed so as to be a predetermined distance from a cutting edge of the first artificial anterior tooth, the predetermined distance being at least 5% of the height of the first artificial anterior tooth in the dental axial direction.

2. The set of artificial teeth of claim 1, wherein the abutting face has one of a circular columnar surface, an elliptical columnar surface, and a conical surface.

3. The set of artificial teeth of claim 1, wherein the abutting face is formed so as to extend up to an area of the first artificial anterior tooth adjacent a basal surface of the artificial anterior teeth.

4. The set of artificial teeth of claim 1, wherein the abutting face extends from a labial side to a lingual side of the first artificial anterior tooth.

5. The set of artificial teeth of claim 1, wherein the abutting face is a rotating body surface, a shape of the rotating body surface being defined by rotating an abutting line on which the abutting face contacts the second artificial anterior tooth about an axis parallel to the dental axis of the first artificial anterior tooth.

6. The set of artificial teeth of claim 1, wherein the first and second artificial anterior teeth are capable of being moved relative to each other such that the position of the contact line is moved to one of a plurality of positions on the abutting face.

7. The set of artificial teeth of claim 1, wherein the first artificial anterior tooth has a shape of a natural tooth on a portion other than the abutting face.

\* \* \* \* \*